(12) United States Patent
Shiramizu

(10) Patent No.: US 9,835,494 B2
(45) Date of Patent: Dec. 5, 2017

(54) TERAHERTZ WAVE PHASE DIFFERENCE MEASUREMENT DEVICE

(71) Applicant: Hitachi High-Technologies Corporation, Minato-ku, Tokyo (JP)

(72) Inventor: Nobuhiro Shiramizu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/116,331

(22) PCT Filed: Sep. 22, 2014

(86) PCT No.: PCT/JP2014/075080
§ 371 (c)(1),
(2) Date: Aug. 3, 2016

(87) PCT Pub. No.: WO2015/118717
PCT Pub. Date: Aug. 13, 2015

(65) Prior Publication Data
US 2017/0010162 A1  Jan. 12, 2017

(30) Foreign Application Priority Data
Feb. 7, 2014  (JP) ................. 2014-021836

(51) Int. Cl.
*G01J 9/02* (2006.01)
*G01N 21/3581* (2014.01)
(Continued)

(52) U.S. Cl.
CPC ............ *G01J 9/02* (2013.01); *G01B 9/02041* (2013.01); *G01B 11/0675* (2013.01); *G01N 21/3581* (2013.01)

(58) Field of Classification Search
CPC ....................................................... G01J 9/02
See application file for complete search history.

(56) References Cited

U.S. PATENT DOCUMENTS

| 2008/0074674 A1 | 3/2008 | Chen et al. |
| 2008/0116374 A1 | 5/2008 | Ouchi et al. |
| 2011/0057109 A1 | 3/2011 | Guo et al. |

FOREIGN PATENT DOCUMENTS

| JP | 2004-101510 A | 4/2004 |
| JP | 2008-116439 A | 5/2008 |

(Continued)

OTHER PUBLICATIONS

International Search Report (PCT/ISA/210) issued in PCT Application No. PCT/JP2014/075080 dated Nov. 11, 2014, with English translation (six (6) pages) "test".

(Continued)

*Primary Examiner* — David Porta
*Assistant Examiner* — Hugh H Maupin
(74) *Attorney, Agent, or Firm* — Crowell & Moring LLP

(57) ABSTRACT

In order to provide a high-sensitivity terahertz wave phase difference measurement system having a high S/N ratio, terahertz interference waves are observed using a half mirror and a movable reference mirror, and the phase difference is calculated, by a terahertz wave generation/detection device that obtains a high S/N ratio by employing a terahertz wave generator for irradiating a non-linear optical crystal with angular phase-matched pump light and seed light, and a terahertz wave detector for irradiating a non-linear optical crystal with angular phase-matched pump light and terahertz waves. In order to match the optical path length of the pump light and the terahertz waves irrespective of the position of the movable reference mirror and the position of a measured object, a first optical delay device, and a second optical delay device that operates in conjunction with movement of a movable reference mirror of a Michelson interferometer, are introduced on the optical path of the pump light.

4 Claims, 6 Drawing Sheets

(51) Int. Cl.
*G01B 9/02* (2006.01)
*G01B 11/06* (2006.01)

(56) References Cited

FOREIGN PATENT DOCUMENTS

| JP | 2009-300279 A | 12/2009 |
| JP | 2011-75583 A | 4/2011 |
| JP | 5155106 B2 | 12/2012 |

OTHER PUBLICATIONS

S. Hayashi et al., "High-peak-power and Tunable Terahertz-wave Generation and Sensitive Detection by using Nonlinear Parametric Conversion", 37th International Conference on Infrared, Millimeter, and Terahertz Waves (IRMMW-THz), Sep. 2012 (three (3) pages).
Takida, Y. et al., "Coherent electro-optical detection of THz-wave generated from synchronously pumped picosecond THz parametric oscillator", 2012, (six (6) pages).
Jun'ichi Shikata et al., "Fourier transform THz-wave spectrometer using THz-wave parametric generation", 2000, pp. 31-36 (with English Abstract).
Takayuki Isogawa et al., "Tomographic Imaging Using Photonically Generated Low-coherence Terahertz Sources", 2012, p. 298.

F I G . 1
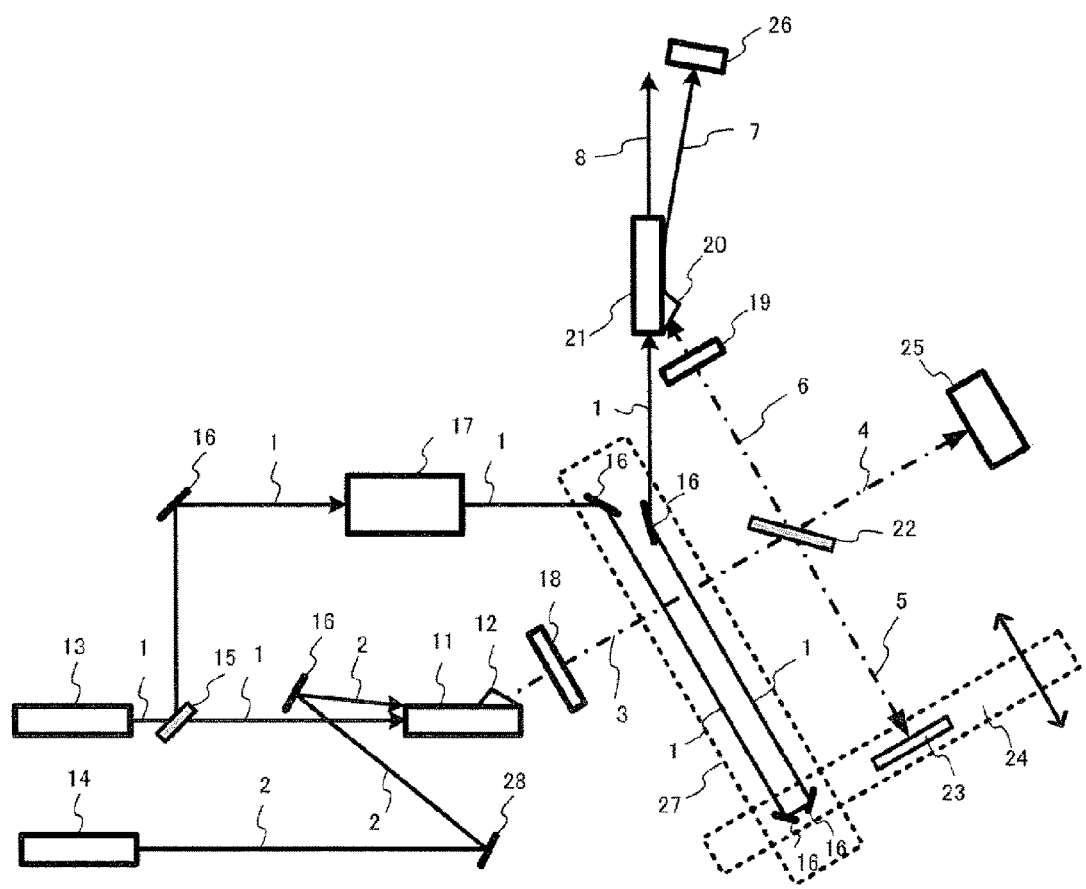

F I G . 2
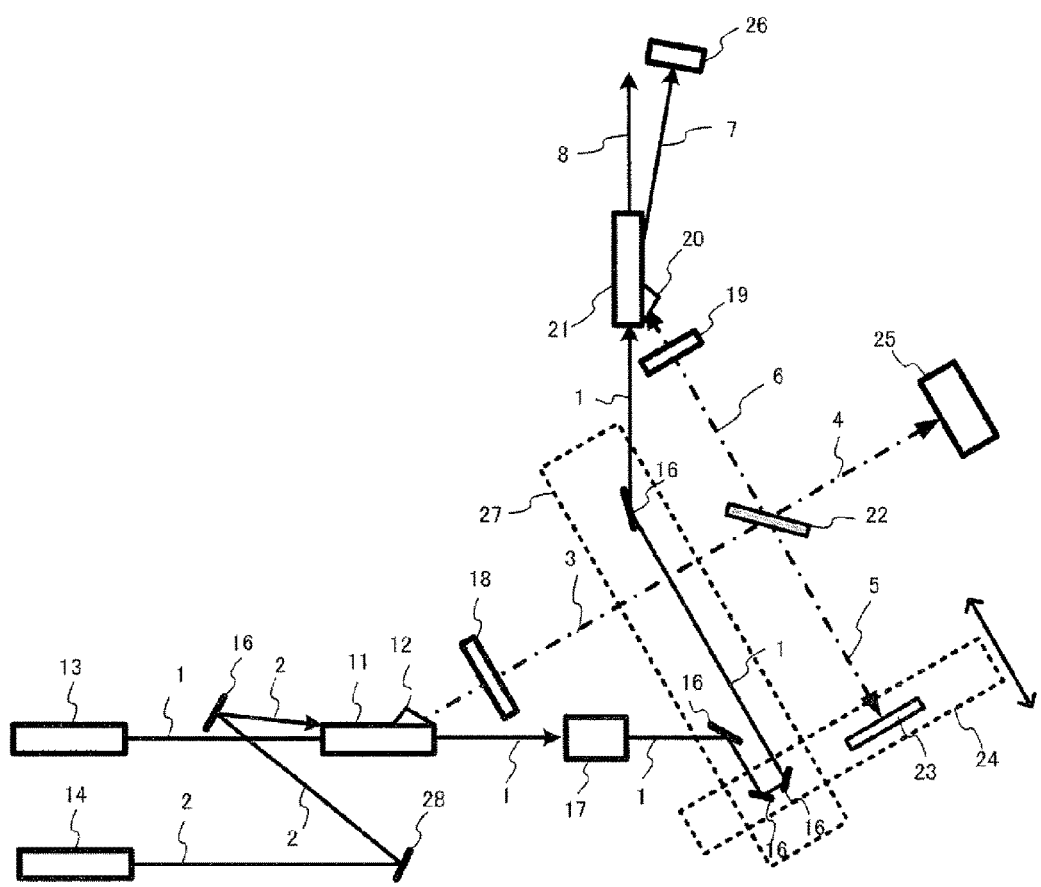

TERAHERTZ WAVE PHASE DIFFERENCE MEASUREMENT DEVICE

TECHNICAL FIELD

The present invention relates to a terahertz wave phase difference measuring system and in particular to a terahertz wave phase difference measuring system configured to detect a phase difference caused by a measured object by applying a terahertz wave to the object and observing a resulting reflected wave or transmitted wave, especially, which device is suitable for non-destructively observing a shape of surface asperities or the like in an object, a thickness of a layer, a film, or the like on an object, or an internal structure, such as a void, or an index of refraction of an object.

BACKGROUND ART

Terahertz wave refers to an electromagnetic wave whose frequency is within a range of 0.1 THz to 10 THz The terahertz wave is excellent in permeability to a wide variety of substances including paper, wood, plastic, and the like as compared with far infrared rays which are electromagnetic waves of higher frequency bands; meanwhile, the terahertz wave is excellent in straight advancing property and resolution as compared with millimeter waves which are electromagnetic waves of lower frequency bands.

The characteristic absorption spectrum of a large number of substances including polymeric compounds, such as sugar and protein, are included in the frequency bands of terahertz waves. By applying a terahertz wave to an object and observing a resulting transmitted wave or reflected wave with these features exploited, an advantage is brought about. The shape or internal structure of the object, the presence or absence of any defect or foreign matter, a difference in material or component, or the like can be non-destructively observed with the object kept in a permeable case. For this reason, it is expected that a wide range of terahertz wave applied science applicable to material inspection, structure inspection, chemical inspection, and the like will be implemented in the future.

In particular, by detecting a phase difference between a terahertz wave reflected at a measured object and a terahertz wave reflected at a metal or the like as a basis, an advantage is brought about. Surface asperities of the object, the thickness of a layer of a layered structure, an internal structure such as a void can be non-destructively observed.

By using terahertz waves of a plurality of frequencies to detect a phase difference between individual frequencies, the thickness of a complicated layer and a complicated internal structure can be observed.

By detecting a difference between the phase of a terahertz wave transmitted through a measured object and the phase of a terahertz wave propagated through a space without any object therein, an index of refraction of a material can be non-destructively observed.

However, the conventional terahertz wave technologies do not have a high output terahertz wave oscillator or a highly sensitive terahertz wave-detector and further methods for generating and detecting a plurality of frequencies of terahertz waves are limited. For this reason, some major problems arise. Practical measured objects are limited to thin films, such as painted films on paintings and works of art, foamed materials excellent in terahertz wave permeability, and the like and it takes a long time for measurements. Because of these problems, it used to be difficult to introduce a terahertz wave technology into a product inspecting apparatus or the like requiring high-speed and high-accuracy measuring performance.

As a conventional terahertz wave phase difference measuring system, for example, a method of generating and detecting a terahertz pulse wave described in Patent Literature 1 is known. Ultrashort pulsed light generated by a femtosecond laser is launched into a photoconductive antenna for generation to generate a terahertz pulse wave. The terahertz, pulse wave and the ultrashort pulsed light are substantially simultaneously launched into a photoconductive antenna for detection. By observing currents produced at the photoconductive antennas, the amount of terahertz pulse waves transferred between the two photoconductive antennas is obtained.

Using this method, a terahertz pulse waveform reflected at a measured object and a terahertz pulse waveform reflected at a metal plate as a reference are observed and delay times of the respective pulse waveforms are calculated. A phase difference between the terahertz waves can be thereby obtained. Shape and roughness on the surface of a measured object and the thickness and index of refraction of each layer as for a layered structure can be measured.

As described in Patent Literature 2, a method of generating a terahertz wave of a narrow hand and detecting the same with a terahertz wave detector of a wide band is known.

In addition, a method described in Non-patent Document 1 is known in which method a nonlinear optical crystal is used both for terahertz wave generation and for terahertz wave detection to achieve generation of a terahertz wave of a narrow band and a high intensity and detection of a terahertz wave with high sensitivity.

CITATION LIST

Patent Literature

PTL 1: Japanese Patent Application Laid-Open No 2004-101510
PTL 2: Japanese Patent No. 5155106

Non-Patent Literature

NPL 1: Shinichiro Hayashi, et al., "High-peak-power and tunable terahertz-wave generation and sensitive detection by using nonlinear parametric conversion," 37th International Conference on Infrared, Millimeter, and Terahertz Waves (IRMMW-THz), September 2012

SUMMARY OF INVENTION

Technical Problem

However, the technology described in Patent Literature 1 uses a terahertz pulse wave having a short pulse width and thus intensity is low and a sufficient S/N ratio cannot be obtained. For this reason, the technology is limited to applications to objects, such as thin films of paint and the like, high in terahertz wave permeability.

In the technology described in Patent Literature 2, a terahertz wave of a narrow band is generated and thus a terahertz wave relatively high in intensity can be obtained. However, since a terahertz wave detector of a wide band, such as a bolometer, is used for detection, a large noise is produced and a sufficient S/N ratio cannot be obtained.

With respect to the technology described, in Non-patent Literature 1, it has been demonstrated that it is possible to generate and detect a terahertz wave of a narrow band and so high an S/N ratio as approximately 100 dB can be obtained in terms of intensity.

However, Non-patent Document 1 does not describe a method for phase detection and unlike the technology described in Patent Literature 2, it is necessary to irradiate both a terahertz wave generator and a terahertz wave detector with pump light. For this reason, a configuration in which a delay time of pump light and a delay time of terahertz are matched with each other to measure a phase of a terahertz wave is required.

FIG. 5 illustrates a concrete problem involved in phase measurement. Pump light is suitable for generating a high-intensity terahertz wave in a short time for prevention of damage to a nonlinear crystal due to heat.

Meanwhile, a certain pulse width is required to narrow the band of a terahertz wave; therefore, a pulse width of approximately 400 ps is used to obtain a band width of 10 GHz or below. In case of pump light, 100 ps or so equivalent to a part of a pulse width is utilized to generate and detect terahertz. A terahertz wave has a pulse width of 100 ps and 50 ps or so equivalent to a part thereof is used for detection.

When pump light and a terahertz wave are not matched with each other in optical path length, as illustrated in the upper tier of FIG. 5, terahertz wave detection light is not produced. In this case, the pulse generation time of pump light is delayed as illustrated in the lower tier of FIG. 5 to overlap the pulses of the pump light and the terahertz wave in the position of a terahertz wave detector. At this time, terahertz wave detection light is produced. Therefore, it is required to match the delay times of pump light and terahertz light with each other within a certain range.

Solution to Problem

In consideration of the above problems, it is an object of the present invention to provide a technology which enables terahertz wave phase difference measurement with a favorable S/N ratio.

For this purpose, in the present invention, a terahertz wave generator and detector described below are used to obtain a high S/N ratio. The terahertz wave generator irradiates a nonlinear optical crystal with pump light and seed light matched in angle and phase with each other. The terahertz wave detector irradiates a nonlinear optical crystal with pump light and a terahertz wave matched in angle and phase with each other. An interferometer is formed of a half mirror and a movable reference mirror and a terahertz interference wave is observed and a phase difference is calculated.

The respective optical path lengths of pump and a terahertz wave are matched with each other regardless of the position of the movable reference mirror or the position of the measured object. For this purpose, a first optical delay device and a second optical delay device interlocked with the movement of the movable reference mirror of the Michelson interferometer are placed on the optical path of pump light.

Advantageous Effects of invention

The following is a brief description of effects obtained by a typical embodiment of the invention disclosed in the present application:

A high-sensitivity and high-accuracy terahertz wave phase difference measuring system can be provided. It is possible to provide a device which is capable of, based on detected phase difference information, detecting the thickness of a layer of a measured object, visualizing a surface shape and an internal structure, and measuring an index of refraction. Since measurements can be made regardless of the optical, path length of a terahertz wave, it is possible to measure a large-sized object and an object placed in an invisible case where a reflection position is unknown.

BRIEF DESCRIPTION OF DRAWINGS

FIG. 1 is a drawing illustrating a first exemplary configuration of a terahertz wave phase difference detection device.

FIG. 2 is a drawing illustrating a second exemplary configuration of a terahertz wave phase difference detection device.

DESCRIPTION OF EMBODIMENTS

Typical Embodiment

Figure 3:
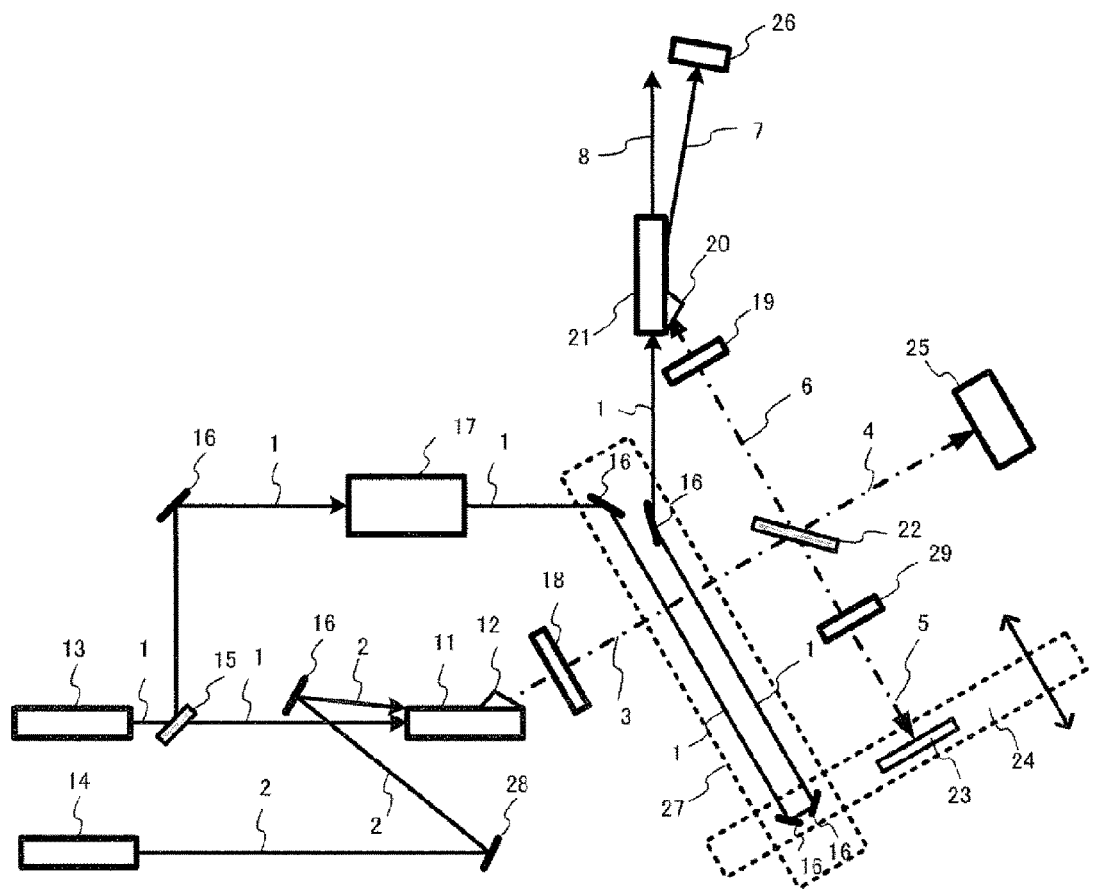
FIG. 3 is a drawing illustrating a third exemplary configuration of a terahertz wave phase difference detection device.

Hereafter, a description will be given to an embodiment of the present invention with reference to the drawings. The device configuration and details of processing operation described below are just examples and any other embodiment can be implemented by combining or replacing this embodiment with an existing technology.

In this embodiment, a light source capable of generating near infrared light is used as a pump light source and a seed light source. Near infrared light generated by the pump light source is designated as pump light and near infrared light generated by the seed light source is designated as seed light.

FIG. 1 illustrates a first exemplary configuration of a terahertz wave phase difference measuring system. Pump light 1 outputted from a pump light pulse laser light source 13 is bifurcated into two directions by a beam splitter 15. The pump light pulse laser light source need not be a single laser light source. In usual cases, an optical, amplifier is connected to the subsequent stage of the laser light source to enhance output to output pump light 1064 nm in wave length, 400 ps in pulse width, 20 mJ/pulse in power, and 100 Hz in pulse repetition frequency.

One beam of the pump light bifurcated by the beam splitter is launched into a terahertz wave generator 11 including a nonlinear optical crystal and a silicon prism 12.

Seed light 2 outputted from a seed light continuous wave laser light source 14 is launched into the terahertz wave generator 11 through an angle phase matching adjustment mirror 28 and a mirror 16. The seed light continuous wave laser light source need not be a single laser light source and usually includes a tunable laser light source and an optical amplifier to output continuous wave seed light 1067 nm to 1075 nm in wave length and 500 mW in power. The angle phase matching adjustment mirror 28 usually includes a diffraction grating and reflects the light at different angles on a frequency-by-frequency basis. When launched into the terahertz wave generator, the angles of incidence of the pump light and the seed light are adjusted to meet such an angle and phase condition that terahertz parametric oscillation is caused in the nonlinear optical crystal.

The angle phase matching adjustment mirror 28 may be a galvano mirror so controlled as to vary the angle on a generated frequency by-generated frequency basis. The silicon prism is bonded to the surface of the crystal to vary an index of refraction for preventing a terahertz wave generated in the nonlinear optical crystal from being reflected at a crystal interface.

A terahertz wave 3 launched from the silicon prism is in an oval beam shape and passes through a cylindrical lens 18 and is thereby turned into a circular beam shape.

The terahertz wave is bifurcated into a first bifurcated terahertz wave 4 and a second bifurcated terahertz wave 5 by a half mirror 22. The first bifurcated terahertz wave is launched into a measured object 25 and a resulting reflected wave is launched into the half mirror 22 again. In cases where the measured object is a material favorable in permeability, the transmitted light may be reflected at a metal mirror.

The second bifurcated terahertz wave is launched into a movable reference mirror 23 and a resulting reflected wave is launched into the half mirror 22 again.

The first bifurcated terahertz reflected wave and the second bifurcated terahertz reflected wave are combined at the half mirror 22, from which an interference wave 6 is outputted. The interference wave 6 is gathered through a convex lens 19 for terahertz waves and launched into a silicon prism 20 bonded to a terahertz wave detector 21. The pump light 1 bifurcated by the beam splitter 15 is launched into a first optical, delay device 17 through a mirror 16.

The first optical, delay device 17 can arbitrarily change an optical path length according to a control signal. Thus even when the position of the measured object is changed or the measuring range in the depth direction is wide, the delay time of pump light can be matched with the delay time of a terahertz wave.

Next, the pump light is launched into a second optical delay device 27 in which two of four mirrors 16 are installed on the same stage 24 as the movable reference mirror 23 and are so configured to be moved in the same direction. Owing to this configuration, even when the movable reference mirror is largely moved, the respective delay times of pump light and a terahertz wave can be matched with each other.

The pump light and the terahertz interference wave are launched into the terahertz wave detector 21 including the nonlinear optical crystal and the silicon prism 20 at such an angle that the light and the wave are matched with each other in angle and phase. As a result, parametric oscillation is caused in the crystal and remaining pump light 8 and terahertz wave detection light 7 whose intensity varies depending on the intensity of a terahertz interference wave are launched at such an angle as to implement angle phase matching depending on the frequency of the terahertz interference wave.

The intensity of the terahertz wave detection light is measured with a photodetector 26, such as a photodiode, a pyroelectric sensor, a bolometer, CCD, or the like. The intensity of the terahertz interference wave is calculated from the intensity of the terahertz wave detection light measured with the photodetector.

A description will be given to a measurement method for phase differences. The intensity of a terahertz interference wave is maximized when the optical path length of a first bifurcated terahertz wave and the optical path length of a second bifurcated terahertz wave are matched with each other. The intensity is minimized when a difference between the optical path length of the first bifurcated terahertz wave and the optical path length of the second bifurcated terahertz wave is equal to ½ wave length.

Instead of a measured object, a reflector such as a metal plate is placed in a position taken as a reference and the stage 24 is scanned and the intensity distribution of the interference wave is measured and recorded for each stage position. An interference waveform is recorded in the same cycle as the wave length of the terahertz wave and is taken as an interference waveform in a standard phase. Subsequently, the measured object is placed and the stage 24 is scanned and an interference waveform is similarly recorded. A difference between the position of the interference waveform, in the standard phase and the position of the interference waveform of the measured object where the intensity is maximized is taken as a phase difference of the terahertz wave. This difference in position is equivalent to a difference between a reference for a distance by which a reflected wave of a terahertz wave reciprocates and a measured object and, is equivalent to twice the deviation from the reference position in the depth direction.

Therefore, a reflecting position of a terahertz wave can be identified from a phase difference. By recording a phase difference while moving a measured object in the horizontal direction or perpendicular direction relative to the optical axis of a terahertz wave, a three-dimensional shape can be visualized. In addition, by recording interference waveforms in a plurality of frequencies and conducting Fourier transformation, a plurality of reflecting positions can be calculated as described in Patent Literature 2.

FIG. 2 illustrates a second exemplary configuration of a terahertz wave phase difference measuring system. Unlike the first exemplary configuration, in this configuration, pump light is launched from the pump light pulse laser light source 13 into the terahertz wave generator 11 without being bifurcated. Sine pump light can be launched into the terahertz wave generator without reducing the intensity of output of the pump light pulse laser light source, the generation intensity of terahertz waves can be enhanced when a light source of the same power is used.

The pump light 1 which passed through the terahertz wave generator is launched into the terahertz wave detector 21 through the first optical delay circuit 17 and the second optical delay circuit 27. Since the intensity of the pump light has been attenuated during the passage through the terahertz wave generator, the intensity of the pump light incident on the terahertz wave detector is reduced. Since a less number of optics are required, an advantage that a measuring installment can be easily built is brought about.

FIG. 3 illustrates a third exemplary configuration of a terahertz wave phase difference measuring system. Unlike the first exemplary configuration, in this configuration, a shutter 29 for terahertz waves is provided on the path of the second bifurcated terahertz wave 5.

The shutter may be configured such that a metal plate is opened or closed, an electrically operated throttle is opened or closed, or the presence or absence of a metal blocking plate placed in a rotary optical filter changer is switched.

Provision of this shutter brings about an advantage. For example, when a measured object is enclosed in an invisible case and the position thereof is unknown, the initial positions of the optical delay devices and the movable reference mirror can be set so that the movable range of the stage is optimized to measure the measured object.

Figure 5:
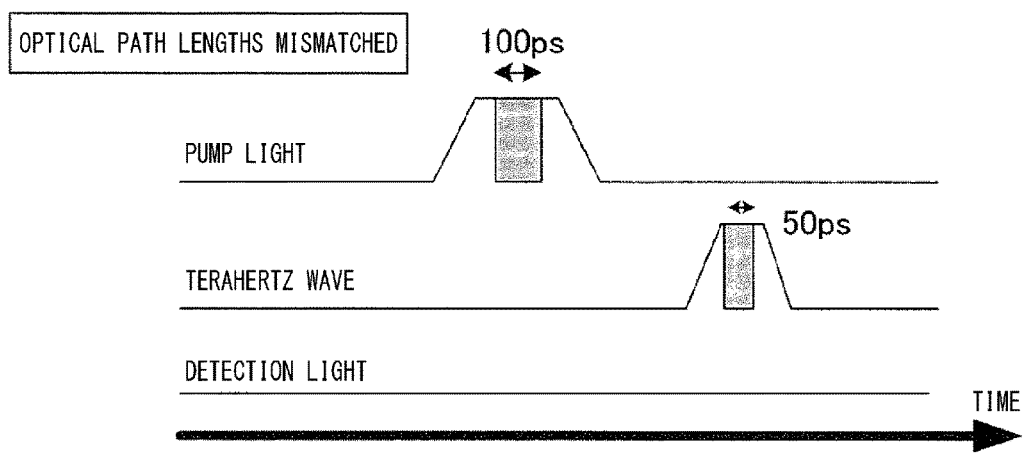
FIG. 5 is a drawing illustrating a problem posed by the respective optical paths length of a terahertz wave and pump light being different from each other.
Figure 5:
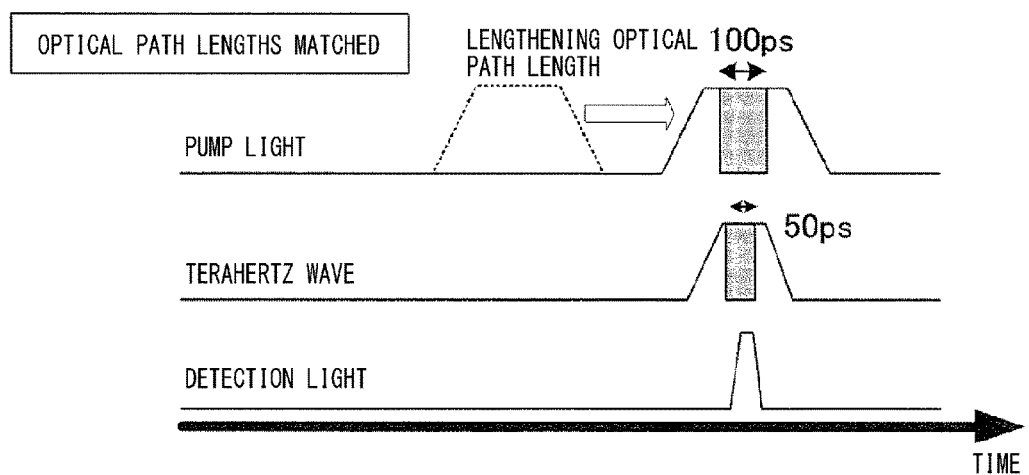
Figure 6:
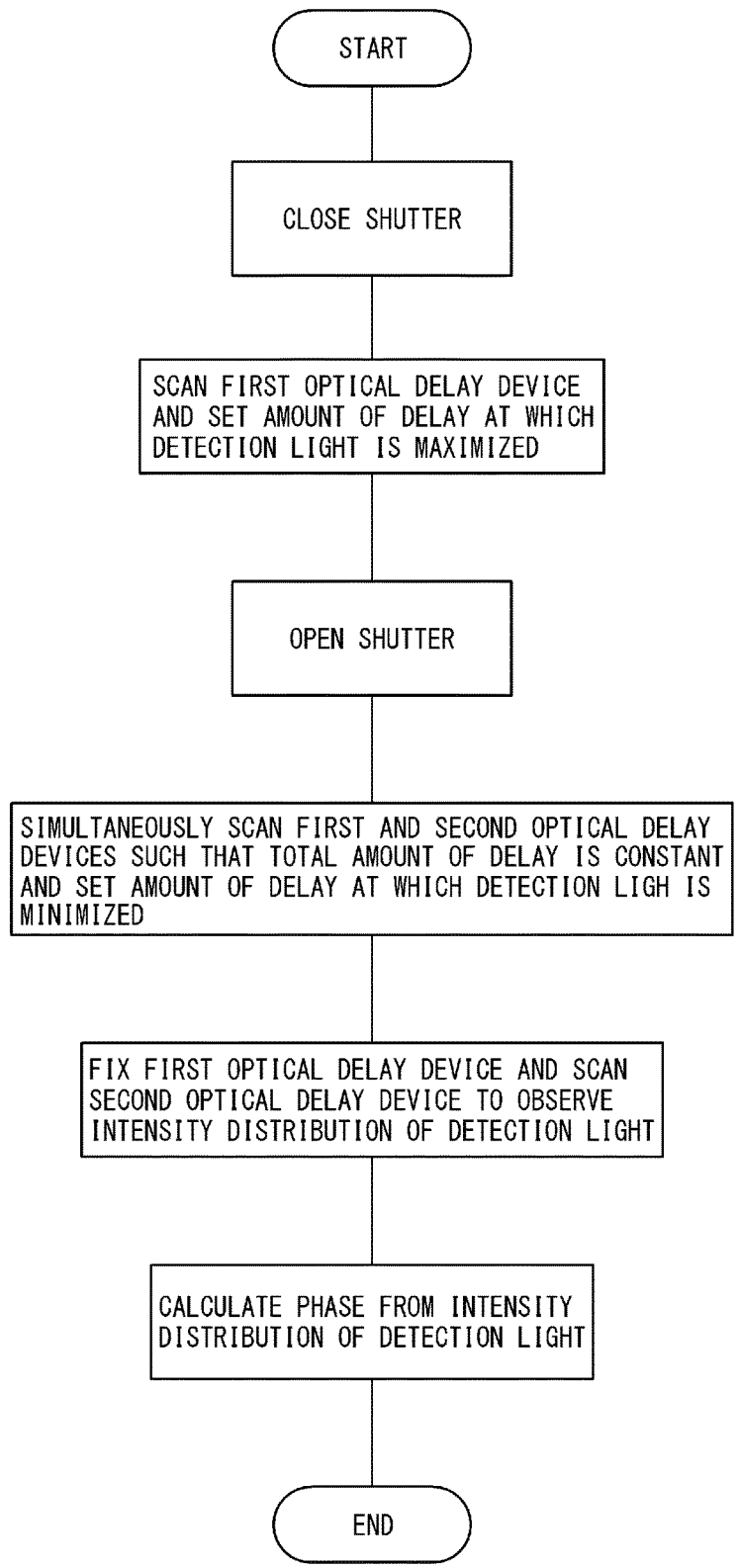
FIG. 6 is a flowchart illustrating an example of a measuring procedure for a phase measuring system.

The flowchart in FIG. 6 illustrates a procedure for this operation. First, the shutter is closed. In this state, the first optical delay device is scanned and a position where terahertz wave detection light is detected with the optical path lengths matched, not with the optical path lengths not matched in illustrated in FIG. 5, is recorded. An optical path length of the first optical delay device is established in the center thereof.

Subsequently, the shutter is opened and the first optical delay device and the second optical delay device are scanned in opposite directions. That is, when optical path length of the first optical delay device is lengthened, the optical path length of the second optical delay device is shortened.

Then it is ensured that the total optical path length of the two optical delay devices is constant. At this time, the intensity of the terahertz interference wave is recorded in each stage 24 position and a stage position where the intensity is maximized is taken as an initial value of the optical path length of the second optical delay device.

Subsequently, only the second optical delay device is scanned forward and backward with the shutter kept open. In the preceding procedure step, the peak position of the interference waveform, that is the state in which the optical path length of the first bifurcated terahertz wave and the optical path length of the second bifurcated terahertz wave are matched with each other has been taken as the initial position. For this reason, by performing scanning ahead of and behind the position, the areas ahead of and behind the reflecting position of a reflector in the depth direction are measured and an optimum stage movable range is obtained. This makes it possible to estimate the position of the measured object hidden in the case from a measured waveform and make an optimal phase difference measurement.

Figure 4:
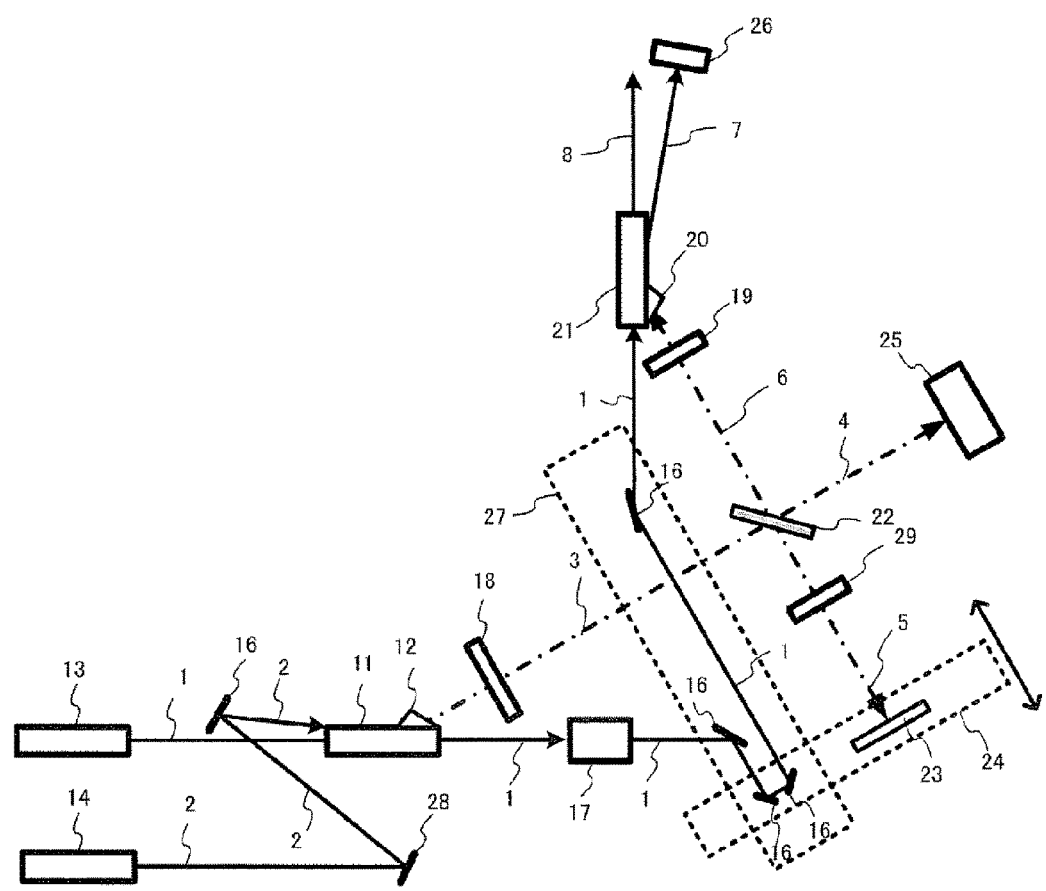
FIG. 4 is a drawing illustrating a fourth exemplary configuration of a terahertz wave phase difference detection device.

FIG. 4 illustrates a fourth exemplary configuration of a terahertz wave phase difference measuring system.

When pump light is not bifurcated as in the second exemplary configuration, the shutter 29 is provided on the path of the second bifurcated terahertz wave 5. As in the third exemplary configuration, a measurement is made according to the flowchart in FIG. 6. This makes it possible to estimate the position of a measured object hidden in a case from a measured waveform and make an optimal phase difference measurement.

REFERENCE SIGNS LIST

1: Pump light,
2: Seed light,
3: Terahertz wave,
4: First bifurcated terahertz wave,
5: Second bifurcated terahertz wave,
6: interference wave obtained by combining first bifurcated terahertz wave and second bifurcated terahertz wave,
7: Terahertz wave detection light,
8: Pump light,
11: Terahertz wave generator,
12: Silicon prism,
13: Pump light pulse laser light source,
14: Seed light continuous wave laser light source,
15: Seam splitter,
16: Mirror,
17: First optical delay device,
18: Cylindrical lens for terahertz waves,
19: Convex lens for terahertz waves,
20: Silicon prism,
21: Terahertz wave detector,
22: Half mirror for terahertz waves,
23: Movable reference mirror,
24: Movable stage,
25: Measured object,
26: Photodetector,
27: Second optical delay device,
28: Angle phase matching adjustment mirror,
29: Shutter for terahertz waves.

The invention claimed is:

1. A terahertz wave phase difference measuring system comprising:
   a pulse laser light source which generates pump light;
   a continuous wave laser light source which generates seed light;
   a terahertz wave generator including a nonlinear optical crystal which launches the pump light and the seed light so as to meet a first angle phase matching condition for generating a terahertz wave and thereby generates a terahertz wave;
   a terahertz wave detector including a nonlinear optical crystal which launches the terahertz wave and the pump light so as to meet a second angle phase mate matching condition for converting the terahertz wave into terahertz wave detection light and thereby generates the terahertz wave detection light;
   a photodetector which detects the detection light;
   a signal processor which converts an output signal of the photodetector into the intensity of a detected terahertz wave and records the intensity;
   a beam splitter which bifurcates pump light from the pulse laser light source into two directions and guides a first bifurcated pump light to the terahertz wave generator and guides a second bifurcate pump light to a first optical delay device;
   the first optical delay device and a second optical delay device which are placed on the optical path of the second pump light and guide the second pump light to the terahertz wave detector;
   a terahertz wave interferometer including a half mirror which bifurcates a terahertz wave launched from the terahertz wave generator into two directions and combines terahertz waves respectively reflected from the two directions and guides the same to the terahertz wave detector, a terahertz wave optical system which applies a terahertz wave bifurcated into a first direction of the half mirror to a measured object and guides a reflected terahertz wave to the half mirror, and a movable reference mirror which reflects a terahertz wave bifurcated into a second direction of the half mirror with any optical path length and guides the same to the half mirror;
   an interlocking mechanism for matching an amount of variation in optical path length of the second pump light of the second optical delay device with an amount of variation in optical path length of a terahertz wave of the movable reference mirror,
   wherein a first optical path length which is a difference between the optical path length of first pump light from the beam splitter to the terahertz wave generator and the optical path length of second pump light going from the beam splitter, passing through the first optical delay device and the second optical delay device, and arriving at the terahertz wave detector and a second optical path length which is the optical path length of a terahertz wave going from the terahertz wave generator, being bifurcated at the half mirror, going in a second direction, being reflected at the movable mirror, passing through the half mirror again, and arriving at the terahertz detector are substantially matched with each other.

2. A terahertz wave phase difference measuring system according to claim 1,
   wherein in the terahertz wave interferometer, a shutter which switches between letting through and blocking a terahertz wave is placed between the half mirror and the movable reference mirror,
   wherein in a first measurement, a second bifurcated terahertz wave is blocked with the shutter, the first optical delay device is scanned, and a position where a peak of detection light is detected is taken as an initial position of the first optical delay device,
   wherein in a second measurement, the shutter is opened to let through a first bifurcated terahertz wave, the first optical delay device and the second optical delay device are scanned such That the optical path length of pump light is constant, and a position where detection light is minimized is taken as an initial position of the second optical delay device, and
   wherein in a third measurement, a first bifurcated terahertz wave is let through, the first optical delay device is fixed, the second optical delay device is scanned, and the intensity of detection light is observed to measure a phase difference between terahertz waves caused by a measured object.

3. A terahertz wave phase difference measuring system comprising:
   a pulse laser light source which generates pump light;
   a continuous wave laser light source which generates seed light;
   a terahertz wave generator including a nonlinear optical crystal which launches the pump light and the seed light so as to meet a first angle phase matching condition for generating a terahertz wave and thereby generates a terahertz wave;
   a terahertz wave detector including a nonlinear optical crystal which launches the terahertz wave and the pump light so as to meet a second angle phase matching condition for converting the terahertz wave into terahertz wave detection light and thereby generates the terahertz wave detection light;
   a photodetector which detects the detection light;
   a signal processor which converts an output signal the photodetector into the intensity of a detected terahertz wave and records the intensity;
   the first optical delay device and a second optical delay device which guide pump light launched from the pulse laser light source and passing through the terahertz generator to the terahertz wave detector;
   a terahertz wave interferometer including a half mirror which bifurcates a terahertz wave launched from the terahertz wave generator into two directions and combines terahertz waves respectively reflected from the two directions and guides the same to the terahertz wave detector, a terahertz wave optical system which applies a terahertz wave bifurcated into a first direction of the half mirror to a measured object and guides a reflected terahertz wave to the half mirror, and a movable reference mirror which reflects a terahertz wave bifurcated into a second direction of the half mirror with any optical path length and guides the same to the half mirror;
   an interlocking mechanism for matching an amount of variation in optical, path length of the pump light of the second optical delay device with an amount of variation in optical path length of a terahertz wave of the movable reference mirror,
   wherein a first optical path length which is the optical path length of pump light going from the terahertz wave generator, passing through the first optical delay device and the second optical delay device, and arriving at the terahertz wave detector and a second optical path length which is the optical path length of a terahertz wave going from the terahertz wave generator, being bifurcated at the half mirror, going in the second direction, being reflected at the movable mirror, passing through the half mirror again, and arriving at the terahertz detector are substantially matched with each other.

4. A terahertz wave phase difference measuring system according to claim 3,
   wherein in the terahertz wave interferometer, a shutter which switches between letting through and blocking a terahertz wave is placed between the half mirror and the movable reference mirror,
   wherein in a first measurement, a second bifurcated terahertz wave is blocked with the shutter, the first optical, delay device is scanned, and a position where a peak of detection light is detected is taken as initial position of the first optical delay device,
   wherein in a second measurement, the shutter is opened to let through a first bifurcated terahertz wave, the first optical delay device and the second optical delay device are scanned such that the optical path length of pump light is constant, and a position where detection light is minimized is taken as an initial position of the second optical delay device, and
   wherein in a third measurement, a first bifurcated terahertz wave is let through, the first optical delay device is fixed, the second optical delay device is scanned, and the intensity of detection light is observed to measure a phase difference between terahertz waves caused by a measured object.

* * * * *